United States Patent [19]
Esmaeili

[11] Patent Number: 5,748,299
[45] Date of Patent: May 5, 1998

[54] METHOD AND SYSTEM FOR DETECTING DIRT ON OPTICAL FIBRES

[75] Inventor: Sasan Esmaeili, Solna, Sweden

[73] Assignee: Telefonaktiebolaget LM Ericsson, Stockholm, Sweden

[21] Appl. No.: 710,187

[22] Filed: Sep. 12, 1996

[30] Foreign Application Priority Data

Sep. 29, 1995 [SE] Sweden ................... 9503365

[51] Int. Cl.$^6$ ........................... G01B 9/02
[52] U.S. Cl. ........................ 356/73.1; 356/345
[58] Field of Search ....................... 356/73.1, 355, 356/345

[56] References Cited

U.S. PATENT DOCUMENTS

| | | | |
|---|---|---|---|
| 4,046,536 | 9/1977 | Smithgall, Sr. | 356/73.1 |
| 4,854,701 | 8/1989 | Noll et al. | |
| 5,185,636 | 2/1993 | Button et al. | |
| 5,323,225 | 6/1994 | Dyott | 356/73.1 |

FOREIGN PATENT DOCUMENTS

0506401 A3   3/1992   European Pat. Off. .

OTHER PUBLICATIONS

European Search Report, dated Jan. 22, 1997.

*Primary Examiner*—Frank G. Font
*Assistant Examiner*—Robert Kim
*Attorney, Agent, or Firm*—Burns, Doane, Swecker & Mathis, L.L.P.

[57] ABSTRACT

When splicing optical fibres, it is necessary that the fibre ends to be spliced together are clean and that no contaminants will be enclosed in the splice after fusing the fibre ends together. The mantle surfaces and sliced surfaces of the fibre ends (2) are illuminated with coherent light (1) wherewith diffraction of the light is indicative of the presence of dirt and dust. Dirt and dust on the mantle surfaces and sliced surfaces of the fibre ends functions as irregular disturbance sources which produce secondary waves having mutually short optical wave differences whose interference forms an irregular pattern with strong contrast that can be recorded on a screen (4) placed behind the fibres. The secondary light fields that are formed when light is diffracted through clean optical fibres are homogenous and their interference forms a periodic and regular pattern. The difference detected between a regular pattern obtained from a clean fibre end and an irregular pattern obtained from a dirty fibre end can then be used in a dirt-detection system.

14 Claims, 3 Drawing Sheets

METHOD AND SYSTEM FOR DETECTING DIRT ON OPTICAL FIBRES

FIELD OF THE INVENTION

The present invention relates to a method of detecting the presence of dirt on an optical fibre (or "fiber") and also to a system for detecting the presence of dirt on an optical fibre. Prior to splicing optical fibres, it is necessary to clean the fibre ends very thoroughly so that no contaminants will be enclosed in the splice that is formed when fusing the ends of the fibres together. The presence of contaminants in a splice will lower the mechanical strength of the splice and possibly dampen the transmission of light in the fibres.

DESCRIPTION OF THE BACKGROUND ART

When splicing optical fibres, the ends of the fibres to be spliced must be clean so that no contaminants will be enclosed in the splice after fusing the fibre ends together. Hitherto, the fibre ends have been cleaned with a washing liquid, optionally in combination with a soft textile material. Any dirt present is liable to burn onto the fibre surfaces prior to splicing, as a result of so-called perfusion.

U.S. Pat. No. 4,854,701, for instance, teaches a system for inspecting the end faces of light waveguides. The system is used to observe the interference pattern formed by measuring light in an air gap between a planar transparent plate and an end face of a light waveguide that lies in abutment with the plate.

SUMMARY OF THE INVENTION

The presence of dirt and dust can be detected, by irradiating the outer cylindrical surface and end faces of the fibres with coherent light. Dirt and dust on the outer cylindrical surface, or mantle, of the fibre ends and their cut faces will function as irregular disturbance sources which generate secondary waves having mutually short optic wave differences, whose interference forms an irregular pattern having significant contrast and capable of being reproduced on a screen placed behind the fibres. The secondary light fields that are formed subsequent to refraction of the light through clean optical fibres are homogenous and their interference generates a periodic and regular pattern. The difference between a regular pattern obtained with a clean fibre end and an irregular pattern obtained with a dirty fibre end is used for dirt detection.

When the end face of an optical fibre is illuminated with laser light, the greater part of the incident light is diffracted geometrically through the fibre, which functions as a powerful cylindrical lens. Due to this lens effect there will be seen essentially a line of light which has the same breadth as the laser beam, when a display screen is placed behind the fibre. However, lateral free propagation of the light immediately adjacent the end face of the fibre is disturbed partly at the transition from air to fibre material on the front side of the fibre and partly at the transition from fibre material to air at the rear side of the fibre. Light waves will be divided explosively as they impinge on a fibre end. Part of the light passes the gap outside the further fibre end without hinderance. A further part of the light is diffracted at the outer cylindrical mantle surface of the fibre and takes another direction. This explosive division of the light forces the light waves to bend laterally through the fibre and in the air space behind the fibre, as can be explained with the aid of Huygens' principle. Bending of the light waves through the fibre causes certain light rays to move in directions other than straight through the fibre. Part of these light rays fall onto the limiting end face of the fibre. This end face delimits the fibre material with a refractive index $n_2$ against a thinner material, air, with a lower refractive index $n_1$, resulting in total reflection; see FIG. 1. The light is thereby divided into two different fields having mutually different phase conditions and in two mutually different wave fronts.

Those light waves contained in a reflection field (R-field) leave the fibre towards air and continue to propagate freely in a space behind the fibre. Those light rays that are not reflected reach the other side, the rear side, of the fibre. Certain of these light waves are again diffracted at the transition to air close to the end face at the rear side of the fibre. However, the waves are not impeded by any obstacle in this case, and spread freely throughout the entire space behind the fibre, these waves forming another light field referred to as Edge-field (E-field); see FIG. 1. Interference between these two light fields forms a regular and periodic diffraction pattern on half the display surface of a screen placed behind the fibre. The diffraction pattern is manifested as a central band of light followed by weaker parallel lines of light (diffraction lines), see FIGS. 2A, B, where FIG. 2A illustrates a clean fibre end and FIG. 2B shows the diffraction pattern that results from RE-interference. The central light line, first intensity maxima, has been blocked out with the aid of a black band so that the weaker diffraction lines can be distinguished. Thus, the diffraction lines are a result of the interference between two secondary wave fronts formed after the diffraction of light through the fibre. Both wave fronts have their sources on the cylindrical fibre mantle according to Huygens' principle.

Minute dust and dirt particles on the mantle surface of the fibre will function as irregular disturbance sources. These disturbance sources transmit secondary waves which are superimposed on the R-field and the E-field and form an irregular pattern that has a much greater contrast than the regular RE-diffraction pattern; see FIGS. 3A, B, where FIG. 3A shows a dirty fibre end and FIG. 3B shows a diffraction pattern deriving from the irregular interference. The central lighter line, first intensity maxima, has been blocked out with the aid of a black band. The difference between this stochastic pattern from a dirty fibre end and the period pattern from a clean fibre end can be detected with the aid of a CCD camera.

DETAILED DESCRIPTION OF ONE EMBODIMENT

Figure 1:
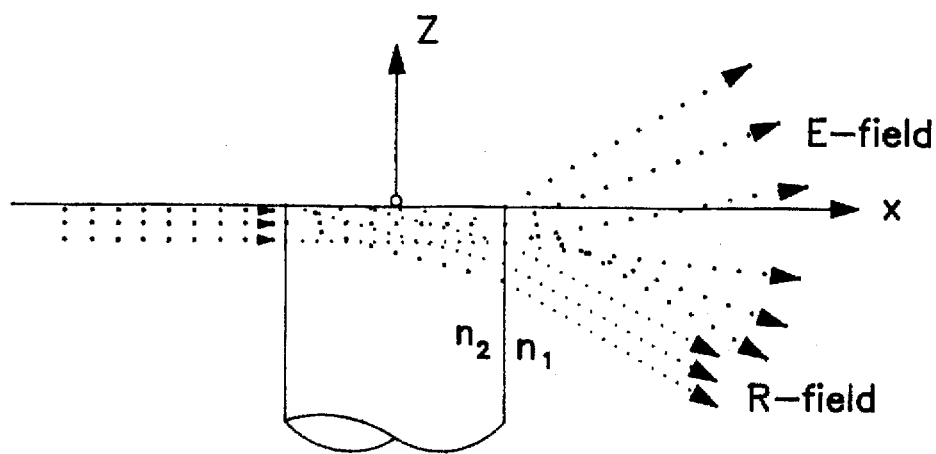
FIG. 1 illustrates lateral spreading of light in accordance with Huygens' principle.
Figure 4A:
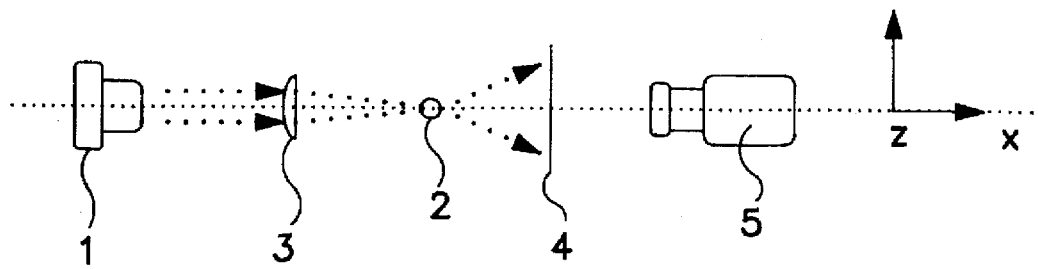
FIGS. 4A, 4B show dirt detection with the aid of laser light in accordance with the invention, from one side and from above respectively.
Figure 4B:
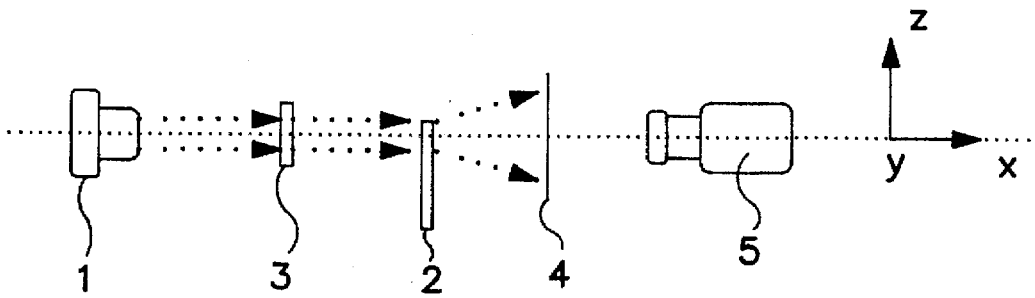
Figure 2A:
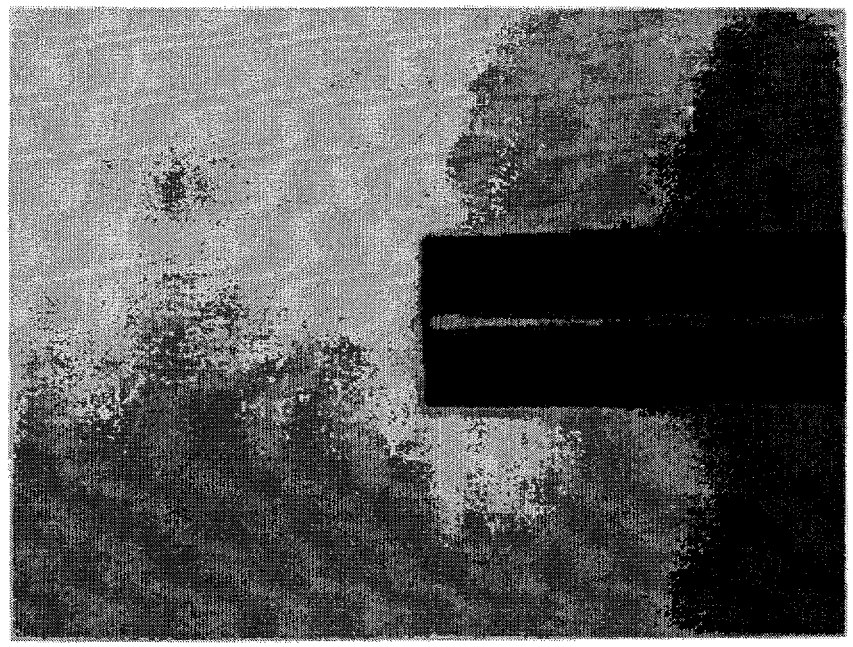
FIGS. 2A, 2B show a clean fibre end and the diffraction pattern from the RE-interference.
Figure 2B:
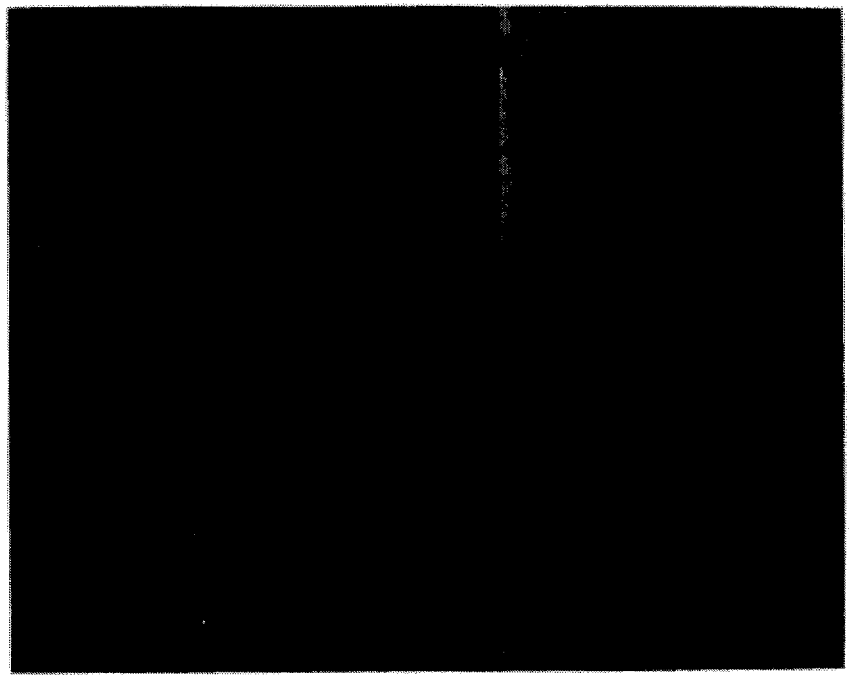
Figure 3A:
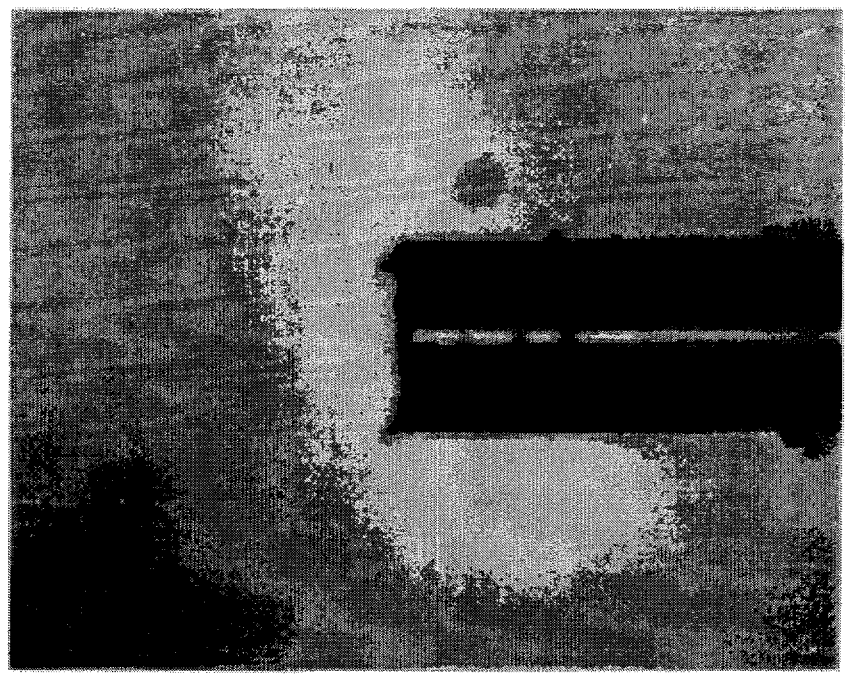
FIGS. 3A, 3B show a dirty fibre end and the diffraction pattern from the irregular interference.
Figure 3B:

FIGS. 4A and 4B illustrate a system for detecting dirt with the aid of laser light from one side and from above respectively. A coherent light source 1, e.g. an HeNe-laser or a diode laser, emits coherent light onto an optical fibre end 2. The light in the fibre end is collected by a collecting lens 3, such as a planar cylindrical lens placed between the light source and said fibre end. The resultant diffraction pattern is imaged on an incoherent semi-transparent screen 4. The area around the fibre end is illuminated orthogonally with the monochromic and coherent light, the diameter of the light beam being chosen so that the light will impinge on at least 0.5 mm of said fibre end. The incoherent semi-transparent screen, the dispersion screen, is placed from the fibre end at a distance of at least 50 mm. A CCD camera 5 images and records the diffraction pattern from the other side of the screen. The cylindrical lens is used to enhance the intensity of the incident light when the intensity is not sufficient to form a clear diffraction pattern. Different cleanliness requirement levels can be defined, by comparing diffraction patterns from clean optic fibre ends. When a computer is connected to the camera, a dirt-warning system can be obtained with the aid of image analysis, e.g. by comparison with reference patterns on clean fibre ends, in which system the computer sends a signal to a monitoring unit when a dirty fibre end is detected, so as to enable appropriate remedial action to be taken. The computer and other equipment may be included in an automatic dirt-warning system provided, e.g., in a fibre-splicing machine, with the use of laser light diffraction to indicate dirt on fibre ends, wherewith a signal is sent to the fibre-splicing machine when dirt is detected on a fibre end, so as to prevent splicing of the dirty fibre end.

I claim:

1. A method of detecting dirt on an optical fibre, comprising the steps of:

illuminating a mantle surface and a cut surface of an optical fibre end with coherent light to create dirt-dependent interference;

imaging the resultant dirt-dependent interference on a screen as an interference pattern; and comparing said interference pattern with a reference image pattern of a clean optic fibre end, wherein a difference in said patterns indicates the presence of dirt.

2. A method according to claim 1, wherein said steps of illuminating and imaging comprise generating with the aid of laser light diffraction said interference pattern that can be recorded on said display screen, and wherein said step of comparing comprises comparing said interference pattern with said reference image pattern of a clean optic fibre end, wherein a difference in said patterns is indicative of the presence of dirt on said fibre end.

3. A method according to claim 2, wherein said steps of illuminating, imaging, and comparing are automatically performed as part of a process for splicing fibres in a fibre-splicing machine, wherein the method further comprises the steps of:

delivering a signal to the fibre-splicing machine when a difference between the imaged interference pattern and the reference image pattern is detected indicative of dirt on said fibre end; and taking action by said machine in response to said signal.

4. A method according to claim 1, wherein said steps of illuminating, imaging, and comparing are automatically performed as part of a process for splicing fibres in a fibre-splicing machine, wherein the method further comprises the steps of:

delivering a signal to the fibre-splicing machine when a difference between the imaged interference pattern and the reference image pattern is detected indicative of dirt on said fibre end; and taking action by said machine in response to said signal.

5. A method according to claim 4, wherein said step of taking action comprises a step of cleaning a dirty fibre optic end.

6. A method according to claim 1, wherein said illuminating step generates two wave fronts when said coherent light impinges on said fibre end, and said dirt-dependent interference is caused by interference between said two wave fronts.

7. A system for detecting dirt on an optical fibre, comprising:

a light source for emitting coherent light which illuminates a fibre end to create dirt-dependent interference;

a screen on which said dirt-dependent interference is recorded to produce an imaged pattern; and means for comparing the imaged pattern with a reference pattern so as to determine the cleanliness of the fibre.

8. A system according to claim 7, wherein the light source is a laser, wherein the imaged pattern is studied and evaluated by said means for comparing.

9. A system according to claim 8, wherein said system is for use in a fibre-splicing machine, wherein the operation of said light source, said screen and said means for comparing is automatic, wherein said system further comprises:

a dirt-warning system which when dirt is detected activates the fibre-splicing machine to take action.

10. A system according to claim 8, wherein said laser comprises one of an HeNe laser and a diode laser module.

11. A system according to claim 7, wherein said system is for use in a fibre-splicing machine, wherein the operation of said light source, said screen and said means for comparing is automatic, wherein said system further comprises:

a dirt-warning system which when dirt is detected activates the fibre-splicing machine to take action.

12. A system according to claim 11, wherein said action taken by said fiber-splicing machine comprises cleaning the end of a dirty fibre.

13. A system according to claim 7, wherein said light source illuminates a mantel surface and a cut surface of the optical fibre end.

14. A method according to claim 7, wherein said dirt-dependent interference is caused by interference of two wave fronts generated when said coherent light impinges said fibre end.

* * * * *